US00PP10985P

United States Patent [19]

Parker et al.

[11] Patent Number: Plant 10,985

[45] Date of Patent: Jun. 29, 1999

[54] IMPATIENS PLANT NAMED '96-009-20'

[75] Inventors: Ronald D. Parker, St. George, Utah; Maryke Cleland, Pomfret Center, Conn.

[73] Assignee: John Bodger & Sons, Co., South El Monte, Calif.

[21] Appl. No.: 08/833,513

[22] Filed: Apr. 7, 1997

[51] Int. Cl.[6] ..... A01H 5/00

[52] U.S. Cl. ..... Plt./317

[58] Field of Search ..... Plt./87.6, 317

[56] References Cited

PUBLICATIONS

GTITM UPOV–ROM Citation for '96–009–20' As Per PBR 97–1175 (CA), Apr. 7, 1997.

*Primary Examiner*—Lynette R. F. Smith
*Assistant Examiner*—Kent L. Bell
*Attorney, Agent, or Firm*—Rothwell, Figg, Ernst & Kurz

[57] ABSTRACT

A new and distinct cultivar of Impatiens hybrid plant, and named '96-009-20' is provided. '96-009-20' is distinct in its unusual shades of orange with red venation, slightly cupped flowers, early flowering, medium green foliage and upright branching growth habit.

1 Drawing Sheet

SUMMARY OF THE INVENTION

This invention relates to a new and distinct Impatiens plant, botanically known as a cultivar derived from a cros between *Impatiens walleriana* and *Impatiens auricoma* and is characterized by the following combination of repeatedly observed traits:

1. Exhibits attractive, single, slightly cupped flowers in abundance,
2. exhibits unusual orange shades with red veination,
3. is early flowering,
4. forms medium green foliage, and
5. exhibits an upright branching growth habit.

ORIGIN AND ASEXUAL REPRODUCTION

Asexual reproduction of this cultivar by stem cuttings taken during November, 1994 at Lompoc, Calif. has demonstrated that the characteristics of the new cultivar as herein described are firmly fixed and are retained through successive generations of such asexual propagation, such reproduction establishing that the plant does in fact maintain the characteristics described in successive generations, The female parent (i.e., the seed parent) was an *Impatiens walleriana* named 'Super Elfin White' unpatented and the male parent (i.e., pollen parent) was an unnamed plant of *Impatiens auricoma.* The cross was made in 1991 and the seedling was selected in 1992. This new cultivar has been identified as *Impatiens* Hybrid '96-009-20'. It is possible that other identification will be adopted in the trade, but the name selected will serve for the purposes hereof.

BRIEF DESCRIPTION OF THE PHOTOGRAPH

The accompanying photograph shows, as nearly true as is reasonably possible, a color illustration of a typical specimen of a plant of the new cultivar. The plant of '96-009-20' was approximately 14 weeks from planting as an unrooted stem (internodal) cutting and was grown in a 10 cm pot.

In the photograph:

FIG. 1 depicts a whole plant including mature in inflorescences.

DETAILED DESCRIPTION OF THE NEW CULTIVAR

Figure 1:
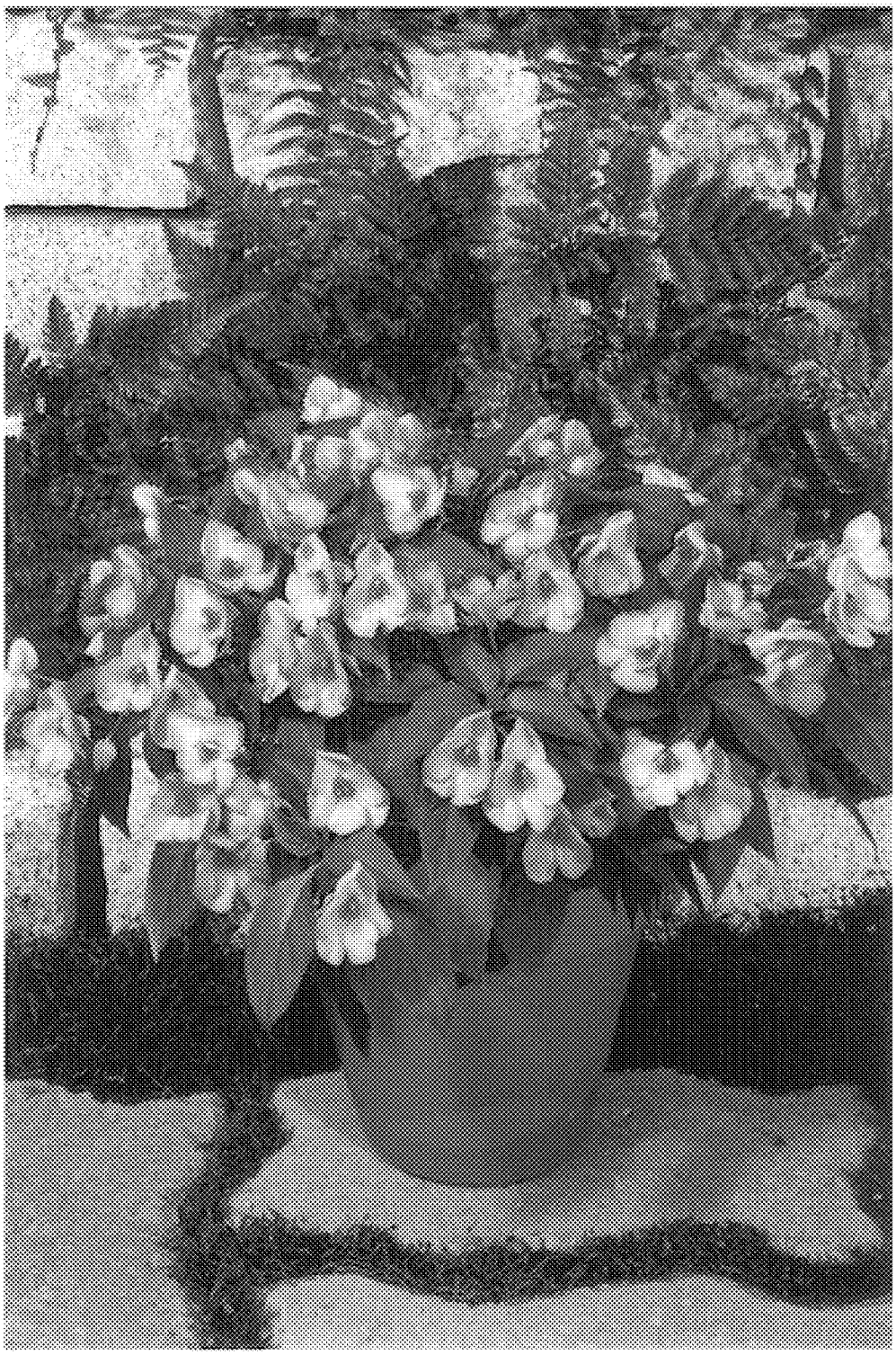

The following observations and measurements describe plants grown near Lompac, Calif. under greenhouse conditions. These observations and measurements were recorded in Spring, 1997 from plants (about 14 weeks from unrooted stem (internodal) cutting) grown in 10 cm pots. Fully developed organs were used for measurements and color descriptions, unless otherwise indicated. Color references are made to The R.H.S. Colour Chart of The Royal Horticultural Society, London, England except where general color terms of ordinary significance are used.

'96-009-20' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Impatiens walleriana* 'Super Elfin White' (unpatented).

*Male parent.*—*Impatiens auricoma*, an unnamed plant.

Propagation:

*Type cutting.*—Stem (internodal) cutting with two nodes and attached leaves.

*Time to initiate roots.*—10–14 days at 70–75 degrees F. with a fully developed root mass at 21 days.

*Rooting habit.*—Fibrous, branching, adventitious root system.

Plant descriptions:

*Form.*—Upright, bush shaped.

*Growth habit.*—Upright branching plant habit with upper leaves and flowers produced in whorls. When grown in a 4 inch pot for 10–12 weeks the height is approximately 4–5 inches and the width is approximately 5 inches.

*Mature growth habit.*—Mature plants grown in 10" pots, eight months of age, reach a mature height of 16–18 inches tall with a spread of 2.5 to 3 feet. The internode length of upper portions of the stem approximately 1 cm long with internodes of lower portions of the stem approximately 2–13 cm long. Stems are reddish and glabrous.

*Vigor.*—Grown in the spring under Lompoc, Calif. conditions in a 70–80 degree Fahrenheit greenhouse; the stem of an actively growing plant elongates approximately 1–1.5 cm in a weeks time.

*Foliage description.*—Leaves are simple. Lower leaves alternate (spirally arranged) with upper leaves arranged in whorls.

*Leaf color.*—Leaf color is green. The upper surface is green group 147A. Under surface is green group 148B with red mottling.

*Petiole.*—Petiole 2.5–4 cm long, with a number of 1–1.5 mm long stipitate glands at the top.

*Leaf shape.*—Lanceolate to elliptic with the base attenuate, the apex acute to acuminate.

*Leaf size.*—3 cm wide×6 cm long.

*Leaf margin.*—Crenate with short glandular appendages.

*Leaf dorsal and ventral surface.*—Glabrous.

*Venation.*—Pinnate, arcuate.

Flowering description:

*Flowering habit.*—Indeterminate, flowering continuously. Flowers develop progressively around the upper leaf whorls.

*Natural flowering season.*—Flowers continuously throughout the year.

*Flowers borne.*—Singly on pedicles 3 cm. long in clusters of 2–7 flowers with a peduncle length of 1.5–2 cm long.

*Quantity of flowers.*—Floriferous. One cluster of 2–7 flowers per leaf occurring progressively around the whorl of leaves so that tight buds to mature blooms are visible at the same time in large numbers.

*Calyx.*—Consists of 3 sepals, one pair of lateral 7 mm wide×10 mm long sepals elliptically shaped, acaute at the tip and one lower 8 mm wide×9 mm long sepal, 5 mm deep, navicular in shape, abruptly constricted into a 2 mm wide×15 mm long tubular incurved spur, with a 44 mm bi-lobed tip.

*Mature bud.*—Ovately shaped, bud is 9 mm wide×12 mm long×12 mm tall. Bud surface is glabrous. Bud color is yellow-green group 145B, sometimes reddish.

*Corolla.*—Consist of 5 petals. Upper dorsal petal is free and lies slightly behind the remaining four petals which are fused into two lateral pairs. The dorsal petal is cucullate, forming a hood that projects forward. As a consequence the upper petal of each lateral united pair is curved (cupped) inward. The upper lateral petals slightly overlap the lower petal of each pair with lower petals lying slightly incurved to flat. The petals of the lateral united pairs are close to equal in size. Upper petals obovate, lower petals oblong to elliptical in shape, entire. Two lower petals exhibit red venation which diffuses onto othe base of the petals creating a red splash over the claw.

*Petals.*—Number of petals 5, with all petals overlapping. Top three petals slightly cupped.

*Petal size.*—Dorsal petal: 12 mm wide×12 mm tall. Upper lateral petals: 15 mm×15 mm long. Lower lateral petals: 13 mm wide×22 mm long.

*Flower color.*—Upper surface: Orange group 26C, with the base of the four lower petals yellow/orange group 23B, outer edges orange group 26C. Under surface: Orange group 26C. The two lower petals exhibit a red venation, 45B, which diffuses into the base of these petals giving a red splash appearance over the claw.

*Flower size.*—Approximately 2 cm wide and 3 cm long.

*Lastingness of individual blooms.*—7–10 days.

*Nectary spur length.*—Approximately 1.5 cm long, orange group 26C.

*Reproductive organs.*—Stamens 5. Anthers: Red-purple fused hood forming one organ that surrounds the pistil. Anthers shed pollen prior to stigma becoming receptive. Pollen: Cream color. Filament color: Yellow/ornage group 21C. Stigma: 5 pointed star, translucent clear, lacking color. Ovary: 5 celled, 6 mm long, green in color.

Disease and insect resistance: No known susceptibility to diseases or insects noted to date.

COMPARISON WITH THE KNOWN CULTIVARS.

When '96-009-20' is compared to *Impatiens walleriana* 'Super Elfin White' (unpatented) it is found that '96-009-20' exhibits and unusual flower color, i.e., shades of orange which do not occur in any *I. walleriana* known to applicants. The flowers of '96-009-20' are cupped and slightly smaller, the plant is taller, has a more upright shape and larger leaves that the 'Super Elfin White' (unpatented). The '96-009-20' plant also has red venation which is not present in the 'Super Elfin White' or any commercially available *I. walleriana* known to applicants.

We claim:

1. A new and distinct cultivar of Impatiens plant named '96-009-20', substantially as described and illustrated herein, characterized particularly as to novelty by its unusual shades of orange with red venation, slightly cupped flowers, early flowering, medium green foliage and upright branching growth habit.

* * * * *